United States Patent [19]

Cottman

[11] 4,414,408

[45] Nov. 8, 1983

[54] PHENOLIC ANTIOXIDANTS

[75] Inventor: Kirkwood S. Cottman, Akron, Ohio

[73] Assignee: The Goodyear Tire & Rubber Company, Akron, Ohio

[21] Appl. No.: 349,358

[22] Filed: Feb. 16, 1982

Related U.S. Application Data

[63] Continuation of Ser. No. 192,583, Sep. 30, 1980, abandoned, which is a continuation of Ser. No. 24,752, Mar. 28, 1979, abandoned, which is a continuation of Ser. No. 525,440, Nov. 20, 1974, abandoned.

[51] Int. Cl.$^3$ ............................................. C07C 69/604
[52] U.S. Cl. ..................................... 560/144; 560/140
[58] Field of Search ................................ 560/140, 144

[56] References Cited

U.S. PATENT DOCUMENTS

| | | | |
|---|---|---|---|
| 2,894,022 | 7/1959 | Havers et al. | 560/144 |
| 2,943,076 | 6/1966 | Havers et al. | 560/144 |
| 3,459,787 | 8/1969 | Weesner | 560/144 |
| 3,637,809 | 1/1972 | Kleiner | 560/144 |
| 3,773,812 | 11/1973 | Schultz | 560/144 |

Primary Examiner—James H. Reamer
Attorney, Agent, or Firm—D. O. Nickey

[57] ABSTRACT

Two antioxidants functioning by different mechanisms are combined chemically into one molecule, allowing optimization of their antioxidant properties.

7 Claims, No Drawings

PHENOLIC ANTIOXIDANTS

This is a continuation application under 37 CFR 1.60, of pending prior application Ser. No. 192,593 filed on Sept. 30, 1980 now abandoned, which is a continuation of Ser. No. 24,752, filed on Mar. 28, 1979, now abandoned, which was a continuation of application Ser. No. 525,440, filed Nov. 20, 1974, abandoned.

The present invention relates to novel compounds useful as antioxidants for organic materials and for their preparation from standard antioxidant compounds.

Many organic materials suffer oxidative degradation, the problem being particularly acute in the rubber and plastics industries where the usefulness of the products are sharply reduced unless antioxidants are incorporated into the material.

Numerous materials have been proposed to function as antioxidants, either singly or in combination with others to provide the necessary protection. Those skilled in this art are aware that a combination of compounds may be used to provide improved oxidative stability. It is well known in the art that certain combinations of antioxidants provide more protection than the sum of the antioxidant actions of the components when used separately. This effect is illustrated in French Pat. No. 1,245,606, British Pat. No. 851,670 and U.S. Pat. No. 3,535,277.

However, a homogenous blending of two or more separate components into polymers is difficult to achieve. The effectiveness of multi-component systems in polymers depends on the homogenous blending of the separate components to give polymer compositions containing certain ratios of the separate components. For example, to obtain the optimum effect of phenol/sulfide combinations the ratio of the two separate stabilizers incorporated into the polymer must be closely controlled. Unequal dispersion of two antioxidants can result in undesirably erratic antioxidant performance in different production batches of polymers. The ratios of the various antioxidants can also be upset by the differing rates of volatility and/or extraction for each individual antioxidant.

It is an object of the present invention to provide a process whereby different antioxidants well known in the art are combined by chemical reaction to increase their antioxidant activity. It is a further object of the invention to provide an antioxidant that is superior in resistance to extraction and volatilization. Further objects will be evident to those skilled in this art as the description proceeds.

The above objects are achieved by chemically combining basic antioxidant types to form one high molecular weight molecule with good antioxidant properties.

The antioxidants of the present invention are made by partially esterifying a polyphenolic antioxidant to a more active form, then combining two molecules of the esterified polyphenolic through a sulfur atom to form the active, high molecular weight antioxidant.

The antioxidants of this invention are a series of reaction products. In many cases a resinous product is obtained. Many of the polyphenolic starting compounds are well known to those skilled in this art.

The antioxidants of this invention can be prepared from partial esters of polyphenols. The term "partial esters" is used to mean esterified polyphenols in which less than all of the phenolic hydroxyl groups of the phenol are esterified.

The above compounds are prepared by reacting (A) polyphenolic compounds containing two or more aromatic rings which each contain phenolic hydroxyl groups with (B) acid halides or other similar derivatives capable of forming unsaturated esters. These products are reacted with hydrogen sulfide or a thiol such as 3-mercapto propionic acid to form the antioxidant compounds of this invention. The polyphenolic starting materials can be initially prepared by methods well known to those skilled in this art or it can be a commercially available polyphenolic. A description of the preparation of some of these polyphenolic compounds can be found in U.S. Pat. Nos. 3,036,138 and 3,305,522.

Polyphenolic compounds which can be used to prepare the antioxidants of this invention have the structural formula

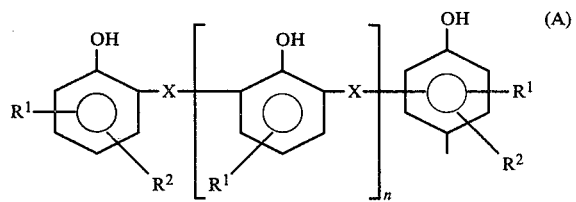

(A)

wherein $R^1$ and $R^2$ are the same or different radicals selected from the group consisting of hydrogen and alkyl radicals containing from 1 to 16 carbon atoms, cycloalkyl radicals containing from 5 to 8 carbon atoms, aralkyl radicals containing from 7 to 12 carbon atoms, and substituted and unsubstituted aryl radicals having from 6 to 12 carbon atoms and $R^1$ preferably contains from 1 to 2 carbon atoms when para to the hydroxyl group, X is the same or different radical selected from the group consisting of (1) polycyclic diene containing from 5 to 20 carbon atoms from which the divalent radicals are prepared or (2) a divalent radical selected from the group consisting of —S—, —O—, —C=O, —CH$_2$—, —S—S— and wherein n is selected from the group consisting of 0 and integers from 1 to 5.

The polyphenolic is reacted with a compound capable of forming an ester having the general formula

(B)

wherein $R^3$ is selected from the group consisting of hydrogen and alkyl radicals having from 1 to 2 carbon atoms, $R^4$ is selected from the group consisting of hydrogen, alkyl radicals having from 1 to 4 carbon atoms, aralkyl radicals having from 7 to 9 carbon atoms, and substituted or unsubstituted aryl radicals having from 6 to 8 carbon atoms, and wherein V is selected from the group consisting of chlorine, bromine and iodine. The amount of esterification of course depends on the molar ratios and steric hindrance of the materials used. Preferably the polyphenolic material is treated with from one mole to 0.1 mole of ester forming compound for each functional hydroxyl group. More preferably at least one functional hydroxyl group per polyphenolic molecule is esterified.

When the polyphenolics and ester forming compounds described herein are reacted in a 1:1 molar ratio, a near theoretical reaction takes place. For example, compounds having the formula (A) wherein n is 0 and X is a divalent radical selected from the group consisting of —S—, —CH$_2$—, and R$^2$ is a hydrocarbon radical of at least 4 carbon atoms (preferably tertiary) and ortho to the hydroxyl group, have only one readily reactive hydroxyl group. Upon esterification of one hydroxyl group, steric hindrance operates to decrease the reaction at the second hydroxyl site. For example, if one mole of methacryloyl chloride is reacted with one mole of 2,2'-methylene-bis-(4-methyl-6-tert.butylphenol) a near theoretical amount of 2-(2-hydroxy-3-tert.butyl-5-methylbenzyl)-4-methylphenyl methacrylate is obtained.

When a polyphenolic according to structure (A) wherein R$^2$ (preferably tertiary) is ortho to the hydroxyl group is reacted with n+2 moles of an ester forming compound having structure (B), less than n+2 moles of compound (B) will react. Normally the number of ester groups reacting with the polyphenolic reactant is not more than n+1.5 or less than n−0.75. When n is 0 the number of ester groups reacting with the polyphenolic is usually not more than 1.5 or less than 0.25.

The esterification reaction can easily take place at atmospheric pressure and temperatures from 0° to the boiling point of the reactants. Preferably temperatures from 0° to 60° C. are used. The ester-forming compound is usually added to the phenolic compound in the presence of a base such as triethylamine, sodium carbonate, pyridine or potassium carbonate.

Once the esterification has taken place, the resulting unsaturated ester is combined through a sulfur atom by reaction with hydrogen sulfide gas in the presence of a solvent such as methanol or toluene.

The joining of the esterified phenol molecules through a sulfur atom can take place in an organic solvent at a temperature of from 0° C. to the boiling point of the solvent. Preferred temperatures are from 25° C. to 65° C. Hydrogen sulfide gas is passed through the solution at a slow rate so that evolution of the gas is at a minimum until the reaction is complete, forming compounds having the general structural formula II. The reaction can be catalyzed by a base such as potassium hydroxide, sodium acetate or sodium methoxide. To produce compounds having general structural formula (II), hydrogen sulfide can be replaced by a thiol such as 3-mercaptopropionic acid or a thiol derivative such as 2-mercaptopropionic acid or methyl, 3-mercaptopropionate.

Compounds of the present invention have a general structural formula selected from the group consisting of

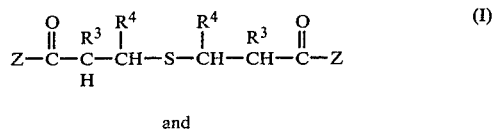

and

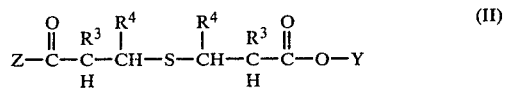

wherein Z is a phenoxy radical derived from the phenolic compound having structure (A) and Y is selected from the group consisting of hydrogen, alkyl radicals having from 1 to 20 carbon atoms, cycloalkyl radicals having from 5 to 8 carbon atoms, aralkyl radicals having from 7 to 12 carbon atoms and substituted aryl radicals having from 6 to 16 carbon atoms and unsubstituted aryl radicals having 6 carbon atoms and R$^3$ and R$^4$ are the same radicals as described above.

Representative examples of the radicals of the above formulas are alkyl radicals such as methyl, ethyl, butyl, pentyl, hexyl and decyl; cycloalkyl radicals such as cyclopentyl, cyclohexyl; alkylaryl radicals such as methylphenyl and hexylphenyl; aryl radicals such as phenyl and naphthyl; aralkyl radicals such as benzyl and 4-methylbenzyl; and halogens such as bromo, iodo and chloro.

Representative examples of cyclic dienes useful in this invention are 1,5-cyclooctadiene, cyclopentadiene, bicyclo[2.2.1]-2,5-heptadiene, 2-methyl bicyclo[2.2.1]-2,5-heptadiene, dicyclopentadiene, pentacyclo[8.2.1.1$^{4,97}$.0$^{2,99}$.0$^{3,98}$]-tetradeca-5,11-diene, and 1,5,9-cyclodedecadiene.

Representative examples of phenolic compounds useful in the practice of this invention include 2,6-bis-(2-hydroxy-3-tert.butyl-5-methylbenzyl)-4-methylphenol; 2,2'-methylene-bis-(4-methyl-6-tert.butylphenol); 2,2'-methylene-bis-(4-ethyl-6-tert.butylphenol); 2,2'-thio-bis-(4-methyl-6-tert.butylphenol); 2-(3,5-ditert.butyl-4-hydroxybenzyl)-4-methylphenol; 2-(3,5-ditert.butyl-4-hydroxybenzyl) phenol; 2-(3,5-ditert.butyl-4-hydroxybenzyl)-5-methylphenol and 2,6-bis-(2-hydroxy-3-tert.butyl-5-ethylbenzyl)-4-ethylphenol, and compounds similar to those prepared in U.S. Pat. Nos. 3,625,874; 3,036,138 and 3,305,522.

Representative examples of ester forming compounds that can be used in the practice of this invention include acryloyl chloride, methacryloyl chloride, cinnamoyl chloride, acryloyl bromide, ethacryloyl chloride, and β-(4-methylcyclohexyl)acryloyl chloride.

Representative examples of phenolic ester compounds useful in the process of the present invention are listed below.

2-(2-hydroxy-3-tert.butyl-5-methylbenzyl)-4-methyl-6-tert.butylphenyl acrylate 2-(2-hydroxy-3-tert.butyl-5-methylbenzyl)-4-methyl-6-tert.butyl phenylmethacrylate 2-(3,5-ditert.butyl-4-hydroxybenzyl)-4-methylphenyl methacrylate 2-(3,5-ditert.butyl-4-hydroxybenzyl)-4-methylphenyl acrylate 2-(2-hydroxy-3-tert.butyl-5-methylphenylthio)-4-methyl-6-tert.butyl phenyl methacrylate 2-(3,5-ditert.butyl-4-hydroxybenzyl) phenyl methacrylate 2,6-bis(2-hydroxy-3-tert.butyl-5-methylbenzyl)-4-methylphenyl methacrylate Representative examples of those compounds having the structural formula (I) produced in the practice of the present invention are bis[2-(2-hydroxy-3-tert.butyl-5-methylbenzyl)-4-isopropyl-6-tert.butylphenyl]thiodipropionate bis[2-(2-hydroxy-3-tert.butyl-5-methylbenzyl)-4-methyl-6-tert.butylphenyl]thiodipropionate bis[2-(3,5-ditert.butyl-4-hydroxybenzyl)-4-methylphenyl]thiodipropionate bis[2-(3,5-ditert.butyl-4-hydroxybenzyl)-phenyl]thiodipropionate Representative examples of compounds having the structural formula (II) produced in the practice of the present invention are 2-(3,5-ditert.butyl-4-hydroxybenzyl)-4-methylphenyl phenyl thiodipropionate 2-(3,5-ditert.butyl-4-hydroxybenzyl)-4-methylphenyl 4-decylphenyl thiodipropionate 2-(3,5-ditert.butyl-4-hydroxybenzyl)-4-methylphenyl benzyl thiodipropionate 2-(2-hydroxy-3-tert.butyl-5-methylbenzyl)-4-methyl-6-tert.butylphenyl cyclohexyl thiodipropionate 2-(3,5-ditert.hexyl-4-hydroxybenzyl)-4-methylphenyl 6-phenylhexyl thiodipropionate 2-(3,5-ditert.butyl-4-hydroxybenzyl)-4-methylphenyl 6-phenylhexyl thiodipropionate 2-(3,5-ditert.butyl-4-hydroxybenzyl)-4-methylphenyl 2-hexylphenyl thiodipropionate 2-(3,5-ditert.butyl-4-hydroxybenzyl)-4-methylphenyl eicosyl thiodipropionate Representative examples of solvents useful when reacting the polyphenolic compound with the ester forming compound are benzene, toluene, xylene, tetrahydrofuran, dioxane, ethanol, benzene and 2-B-ethanol. Representative examples of useful solvents for the reaction of the phenolic esters of this invention with hydrogen sulfide are methanol, ethanol, isopropynol, benzene, toluene, xylene and tetrahydrofuran.

Representative examples of catalysts useful in reacting phenolic esters of the present invention with hydrogen sulfide are sodium hydroxide, sodium methoxide, sodium acetate and potassium hydroxide.

The polyphenolic compounds described in this invention can be reacted with the ester forming compounds in a ratio as described above. Preferably at least one mole of ester forming compound is reacted with one mole of polyphenolic compound. Two esterified polyphenolic compounds are joined by reaction with hydrogen sulfide to form structure (I). The esterification can be partial and can vary depending on the steric hindrance of the individual molecule. All such compounds will be effective in the present invention.

The polymers that may be conveniently protected by the compounds described herein are vulcanized and unvulcanized polymers susceptible to oxygen degradation, such as natural rubber, balata, gutta percha and rubbery synthetic polymers containing carbon to carbon double bonds. Representative examples of the synthetic polymers used in the practice of this invention are polychloroprene; homopolymers of a conjugated 1,3-diene such as isoprene and butadiene with up to 40 percent by weight of at least one copolymerizable monomer such as styrene and acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene. The precise amount of the age resisters which is to be employed will depend somewhat on the nature of the polymer and the severity of the deteriorating conditions to which the polymer is to be exposed. In unsaturated polymers such as those made from conjugated dienes, the amount of age resister necessary is greater than that required by a saturated polymer such as polyethylene.

Generally the stabilizers of this invention are employed from about 0.0005 percent to about 10 percent by weight of the stabilized composition, although this will vary with the particular polymer. A particularly advantageous range is from about 0.025 percent range to about 1.5 percent. The compounds are especially useful for the stabilization of polyethylene and polypropylene. The antioxidants of the present invention have a high molecular weight which makes them less volatile and less easily extracted from the polymer than lower molecular weight antioxidants.

A polymer composition will usually contain other compounding materials such as additives and reinforcing materials used with vulcanized rubber products. Representative examples of such additives are metal oxides, reinforcing agents, pigments, fillers, softening agents, other antioxidants, plasticizing agents, curing agents and the like.

The equipment necessary in synthesizing the compounds of this invention is well known to those in this art. The following are examples of typical runs made to produce the antioxidants of this invention. All parts and percentages given are by weight unless otherwise indicated.

Example 1 describes the preparation of a typical polyphenolic antioxidant. Examples 2, 3 and 4 describe various levels of esterification of the polyphenolic. The remainder of the examples describe the joining of the unsaturated esters with hydrogen sulfide to form the substituted thiodipropionate.

EXAMPLE 1

Three hundred and twenty four grams of p-cresol and $5\frac{1}{2}$ grams of boron trifluoride etherate were added to a one liter three necked flask with thermometer, water condenser and agitator and heated to 90° C. One hundred thirty two grams of dicyclopentadiene were added dropwise over a twenty minute period. The solution was stirred for fifteen additional minutes. The unreacted p-cresol was distilled off at a reactor temperature of 190° C. and 15 millimeters of mercury. The residue weighed 300 grams. The resin was dissolved in 300 milliliters of toluene. Twenty five grams of toluene sulfonic acid was added followed by as much isobutylene as was possible between 60° C. and 70° C. The reaction product was neutralized with 25 grams of sodium carbonate in aqueous solution. The aqueous layer was decanted and two grams of dry sodium carbonate was added. The volatiles were distilled off at a reactor temperature of 180° C. and 15 milliliters of mercury. The weight residue was 360 grams with a hydroxyl number of 347. The properties of this compound are described in U.S. Pat. No. 3,305,522.

EXAMPLE 2

Using the same equipment as was described in Example 1, 150 grams of the resin prepared as in Example 1 was dissolved in 150 milliliters of tetrahydrofuran along with 30 grams of triethylamine. Nineteen grams of acryloyl chloride was added over a seven minute period at a temperature below 35° C. After stirring for thirty minutes, 150 milliliters of toluene was added. The reaction product was hot water washed. Volatiles were removed at a reactor temperature of 180° C. under vacuum in the presence of one gram of dry sodium carbonate. The product had a hydroxyl number of 313.

EXAMPLE 3

One hundred fifty grams of a product prepared as described in Example 1 was dissolved in 150 milliliters of tetrahydrofuran and 55 grams of triethylamine. Thirty-nine grams of acryloyl chloride was added over a 15 minute period at a temperature of between 25° C. and 33° C. The reaction product was stirred for 50 minutes and diluted with 150 milliliters of toluene. The mixture was hot water washed. Two grams of dry sodium carbonate was added and volatiles were removed from the reaction product at a reactor temperature of 170° C. under vacuum. The product had a hydroxyl number of 262.

EXAMPLE 4

One hundred fifty grams of a product prepared as described in Example 1 was dissolved in 150 milliliters of tetrahydrofuran and 75 grams of triethylamine. Fifty-eight grams of acryloyl chloride was added over a 25 minute period at a temperature of between 22° C. and 32° C. The reaction product was stirred for 45 minutes at 50° C. and then diluted with 200 milliliters of toluene. After reacting an additional two hours, the reaction product was washed with water. Two grams of sodium carbonate was added and volatiles were removed from the reaction product at a reactor temperature of 180° C. under vacuum. The product had a hydroxyl number of 215.

EXAMPLE 5

One hundred grams of the product prepared as in Example 2 and 6 grams of sodium acetate catalyst were slurried in 500 milliliters of methanol and 100 milliliters of toluene in a one liter flask equipped with thermometer, stirring blade, water condenser and gas inlet tube. Hydrogen sulfide gas was added at a rate such that it was not evolved for 3½ hours at a temperature of 50° C. to 55° C. The 1:1 mole ratio of the reaction product of Example 1 and acryloyl chloride/H$_2$S adduct were separated from the volatiles at a reactor temperature of 180° C. and 35 milliliters of mercury. The product had a sulfur percentage of 2.24.

Preferably the sodium acetate catalyst is removed from the product by water washing or filtration while in solution. Solvents such as benzene or toluene can be used.

EXAMPLE 6

One hundred grams of the product as prepared in Example 3 was dissolved in 400 milliliters of 2-B-alcohol and 100 milliliters of toluene followed by 6 grams of sodium acetate. Hydrogen sulfide gas was added at a rate such that it was not evolved for 6 hours at a temperature of 55° C. to 65° C. The flask content was then distilled to remove volatiles at a reactor temperature of 150° C. under vacuum. The H$_2$S adduct of the 1:2 mole ratio reaction product of Example 1 and acryloyl chloride had a sulfur content of 2.64 percent. The catalyst is preferably removed as described in Example 5.

EXAMPLE 7

Using the same equipment as described in Example 5 above, 100 grams of the resin prepared in Example 4 was dissolved in 400 milliliters of 2-β-alcohol and 150 milliliters of toluene along with 6 grams of sodium acetate. Hydrogen sulfide gas was added at a rate such that it was not evolved for 5¼ hours at a temperature of 60° C. to 70° C. The reaction product was heated to a reactor temperature of 75° C. under vacuum in order to remove the methanol. Five hundred milliliters of toluene were added. The resin did not totally dissolve at 70° C. so the sodium acetate was not removed. The toluene was distilled off at a reactor temperature of 160° C. under vacuum. The product was a 1:3 mole ratio of the reaction product of Example 1 and acryloyl chloride reacted with H$_2$S and had a sulfur content of 2.98 percent.

EXAMPLE 8

One hundred sixteen grams of 2,2'-methylene-bis-(4-methyl-6-tert.butylphenol) was dissolved in 100 milliliters of tetrahydrofuran and 42 grams of tri-ethylamine. Over a 45 minute period, 33.7 grams of acryloyl chloride was added at 30° C. The contents of the flask were stirred for 1½ hours and then diluted with 150 milliliters of toluene. The flask content was washed with water. The remaining traces of water were distilled off after the final decant, and the reaction product was filtered. Volatiles were removed from the filtrate at a reactor temperature of 65° C. During distillation the product began to crystallize. Petroleum ether containing a small amount of methanol was added to recrystallize the product. The product, 2-(2-hydroxy-3-tert.butyl-5-methylbenzyl)-4-methyl-6-tert.butyl phenyl acrylate, had a melting point of 128° C. to 131° C.

EXAMPLE 9

Using the same equipment as described in Example 5 above, 60 grams of the 2-(2-hydroxy-3-tert.butyl-5-methylbenzyl)-4-methyl-6-tert.butyl phenyl acrylate from Example 8 and 5.2 grams of sodium acetate were dissolved in 400 milliliters of methanol. The reaction vessel was heated to 60° C. and hydrogen sulfide gas was added at a rate such that it did not evolve for a period of 8½ hours. Thin layer chromatography indicated that all the product of Example 8 had reacted. The flask contents were heated to 65° C. under vacuum to remove methanol. Benzene was added and the product was washed with hot water. Volatiles were removed by distillation at 60° C. under vacuum yielding a white waxy solid. The product was characterized as bis[2-(2-hydroxy-3-tert.butyl-5-methylbenzyl)-4-methyl-6-tert.butylphenyl]thiodipropionate with a sulfur content of 4.1 percent. An alternate method of preparation is set out in Example 12.

EXAMPLE 10

One hundred ten grams of 2-(3,5-di-tert.butyl-4-hydroxybenzyl)-4-methylphenol was dissolved in 150 milliliters of tetrahydrofuran and 45 grams of triethylamine. Over a 20 minute period, 43.4 grams of acryloyl chloride was added below 35° C. The reaction product was stirred 2½ hours and then diluted with 250 milliliters of toluene. A hot water wash followed. Volatiles were distilled from the product at a reactor temperature of 75° C. under vacuum yielding a product weighing 146 grams. The product was 2-(3,5-ditert.butyl-4-hydroxybenzyl)-4-methylphenylacrylate.

EXAMPLE 11

One hundred grams of the 2-(3,5-di-tert.butyl-4-hydroxybenzyl)-4-methylphenylacrylate prepared in Example 10 and 9 grams of sodium acetate were dissolved in 550 milliliters of methanol. Hydrogen sulfide gas was added at 55° C. at a rate such that it was not evolved for 6½ hours. The methanol was distilled off and 600 milliliters of benzene were added. The flask contents were washed with hot water, and the benzene was distilled from the flask contents at 80° C. at 22 millimeters of mercury. The weight of the product was 108 grams with a sulfur content of 4.45 percent. The product was bis[2-(3,5-di-tert.butyl-4-hydroxybenzyl)-4-methylphenyl]thiodipropionate. An alternative method for isolating the product is to precipitate it by cooling the methanol solution. The white powder, after washing with water and drying, had a melting point of 139° C. to 142° C.

EXAMPLE 12

Using the equipment described in Example 1, 50 grams of the resin prepared in Example 2 and 3 grams of sodium acetate were dissolved in 300 milliliters of 2 percent B-alcohol (benzene in ethanol). Fifteen grams of 3-mercapto propionic acid were added and allowed to react for 12 hours at 40° C. to 50° C. The solvent was then distilled off under vacuum at a reactor temperature of 80° C. Two hundred milliliters of toluene were then added to dissolve the resin. The flask contents were washed several times with hot water. One gram of $Na_2CO_3$ was added. Volatiles were removed from the product by distillation at a reactor temperature of 80° C. and 12 millimeters of mercury. The product weighed 56 grams and contained 4.3 percent sulfur.

In the past, antioxidant effects have been obtained by the simple mechanical mixing of antioxidants that functioned by different mechanisms. For example, British Pat. No. 1,078,772 described mixing dilauryl thiodipropionate and di-tert.butyl p-cresol, but such antioxidant systems are much more subject to extraction and volatilization than the large chemically combined molecules described herein.

The compounds of this invention have been evaluated by oxygen absorption yielding the data revealed below. The control compound is described in U.S. Pat. No. 3,305,522. The amount of time in hours to absorb one percent oxygen was determined and is listed in Table I. The testing procedure is described in detail in Industrial and Engineering Chemistry, Vol. 43, page 456 (1951) and Industrial and Engineering Chemistry, Vol. 45, page 392 (1953).

TABLE I

| Oxygen Absorption Data | |
|---|---|
| Antioxidant (1.0 part) | Hours to Absorb 1% $O_2$ in SBR-1006 |
| No antioxidant control | <20 |
| Example 1 | 366 |
| Example 2 | 398 |
| Example 3 | 389 |
| Example 4 | 328 |
| Example 5 | 449 |
| Example 6 | 468 |
| Example 7 | 452 |
| Example 8 | 315 |
| Example 9 | 652 |
| Example 11 | 559 |
| Example 1 (control) | 340 |

Examples 2, 3 and 4 are the respective controls for Examples 5, 6 and 7. Example 8 is a control for Example 9.

In Tables II and III the symbols used measure various coloring characteristics in polypropylene. The color characteristics were determined as defined below.

The symbol Rd is a measure of reflectance on the Gardner Colorimeter based upon a MgO standard given the value of 91.1. This value indicates position along a neutral color axis from black to white with high values indicating high reflectance or brightness.

The symbol "a" is an expression of the dominant colors of red (if a positive value) and of green (if a negative value). Intensity of either color is indicated by the magnitude of the value regardless of sign. The standard is magnesium oxide given the value of 0.0.

The symbol "b" is an expression of the dominant colors of yellow (if a positive value) and of blue (if a negative value). Intensity of either color is indicated by the magnitude of the value regardless of sign. The standard is magnesium oxide given the value of 0.0.

The color index is a measure of the total polymer color characteristics and is calculated by RD/(a+b).

TABLE II

| Color Characteristics | | | | | | |
|---|---|---|---|---|---|---|
| SBR* | 100.00 | | | | | |
| Zinc Oxide | 10.00 | | | | | |
| Titanium Dioxide | 10.00 | | | | | |
| 40% Dicumyl Peroxide | 2.25 | | | | | |
| Example 11 | 1.50 | | | | | |
| Example 5 | | 1.50 | | | | |
| Example 6 | | | 1.50 | | | |
| Example 7 | | | | 1.50 | | |
| Example 1 | | | | | 1.50 | |
| 3,3'-Dilaurylthio Dipropionate | | | | | | 1.50 |
| Original - Tinting | | | | | | |
| Rd | 87.6 | 86.7 | 86.7 | 87.8 | 88.6 | 88.6 |
| a | −0.7 | −0.4 | −0.6 | −0.6 | −0.6 | −0.7 |
| b | +4.4 | +4.7 | +4.9 | +5.1 | +4.4 | +3.9 |
| Color Index | 17.2 | 17.0 | 15.8 | 15.4 | 17.7 | 19.3 |
| Fade-O-Meter Exposed 120 Hours - Discoloration | | | | | | |
| Rd | 74.8 | 84.8 | 86.0 | 86.0 | 85.4 | 87.4 |
| a | −2.0 | −1.8 | −1.1 | −0.8 | −3.1 | −0.8 |
| b | +24.7 | +9.4 | +6.7 | +6.7 | +15.1 | +5.6 |
| Color Index | 2.80 | 7.57 | 11.02 | 11.57 | 4.69 | 13.67 |
| Fade-O-Meter Exposed 120 Hours, Coated - Stain | | | | | | |
| Rd | 89.6 | 90.6 | 91.2 | 90.9 | 91.0 | 91.4 |
| a | −0.7 | −0.3 | −0.2 | −0.2 | −0.2 | −0.1 |
| b | +6.0 | +4.6 | +4.1 | '4.2 | +4.9 | +4.1 |
| Color Index | 13.40 | 18.51 | 21.20 | 20.70 | 17.84 | 21.80 |

*Non-pigmented, 0% bound styrene, fatty acid emulsified

TABLE III

| Antioxidant Evaluation In Polypropylene | | | | | | | |
|---|---|---|---|---|---|---|---|
| Polypropylene* No Antioxidant | 100.0 | | | | | | |
| Example 11 | | 0.30 | | | | | |
| Example 5 | | | 0.30 | | | | |
| Example 6 | | | | 0.30 | | | |
| Example 7 | | | | | 0.30 | | |
| Example 9 | | | | | | 0.30 | |
| Example 1 | | | | | | | 0.30 |
| Original | | | | | | | |
| Rd | | 56.6 | 56.0 | 52.1 | 50.2 | 47.0 | 59.3 | 47.8 |
| a | | −1.0 | −1.2 | −1.4 | −1.5 | −1.4 | −1.0 | −1.5 |
| b | | +5.8 | +7.3 | +12.3 | +11.7 | +16.1 | +6.7 | +15.5 |
| Color Index | | 8.3 | 6.6 | 3.8 | 3.8 | 2.7 | 7.7 | 2.8 |
| Oven Aged 1 Day at 140° C. | | | | | | | |

TABLE III-continued

| Antioxidant Evaluation In Polypropylene | | | | | | | |
|---|---|---|---|---|---|---|---|
| Rd | 53.9 | 51.9 | 50.5 | 47.6 | 43.3 | 54.4 | 39.5 |
| a | −1.2 | −2.6 | −1.5 | −1.5 | −0.1 | −1.9 | −0.3 |
| b | +6.7 | +12.8 | +12.2 | +15.2 | +18.7 | +11.3 | +26.3 |
| Color Index | 6.8 | 3.4 | 3.7 | 2.9 | 2.3 | 4.1 | 1.48 |
| Oven Aged 3 Days at 140° C. | | | | | | | |
| Rd | Crazed | 46.2 | 48.9 | 47.4 | 46.5 | 45.8 | 33.8 |
| a | Crazed | −2.5 | −2.0 | −1.4 | −1.3 | −2.4 | +2.7 |
| b | Crazed | +21.9 | +19.4 | +18.8 | +20.8 | +26.0 | +29.4 |
| Color Index | Crazed | 1.90 | 2.3 | 2.3 | 2.1 | 1.61 | 1.05 |
| Oven Aged 10 Days at 140° C. | | | | | | | |
| Rd | Failed | 41.5 | 42.5 | 42.1 | 42.5 | 37.6 | 29.4 |
| a | Failed | −0.1 | 0.0 | −0.3 | 0.0 | +2.4 | +9.0 |
| b | Failed | +23.6 | +23.7 | +21.5 | +21.9 | +26.8 | +31.3 |
| Color Index | Failed | 1.75 | 1.88 | 1.97 | 1.94 | 1.29 | 0.73 |
| Days to Failure at 140° C. | | | | | | | |
| Craze | 2 | 106 | 62 | 70 | 70 | 59 | 38 |
| Destruction | 6 | 117 | 72 | 90 | 83 | 70 | 46 |

*Polypropylene homopolymer molding powder - Hercules Chemical Co.

Some compounds of this invention were also tested in a compound formula. The data obtained are given in Table IV.

TABLE IV

| Antioxidant Evaluation | | | | | | | |
|---|---|---|---|---|---|---|---|
| Pale Crepe | 100.00 | | | | | | |
| Zinc Oxide | 15.00 | | | | | | |
| Stearic Acid | 1.50 | | | | | | |
| Titanium Dioxide | 45.00 | | | | | | |
| Champion Hard Clay | 10.00 | | | | | | |
| Ultramarine Blue | 0.20 | | | | | | |
| Benzothiazyl Disulfide | 0.80 | | | | | | |
| Diphenyl Guanidine | 0.20 | | | | | | |
| 80% Insol. Sulfur | 3.00 | | | | | | |
| No Antioxidant | | | | | | | |
| Example 11 | | 0.75 | | | | | |
| Example 5 | | | 0.75 | | | | |
| Example 6 | | | | 0.75 | | | |
| Example 7 | | | | | 0.75 | | |
| Example 9 | | | | | | 0.75 | |
| 3,3′-Dilaurylthio Dipropionate | | | | | | | 0.75 |
| Monsanto Rheometer at 280° F., 3° arc, low frequency | | | | | | | |
| High | 65.2 | 62.0 | 63.1 | 64.6 | 65.6 | 63.6 | 64.1 |
| Low | 4.1 | 4.3 | 3.8 | 3.8 | 3.4 | 3.9 | 3.9 |
| Δ | 61.1 | 57.7 | 59.3 | 60.8 | 62.2 | 59.7 | 60.2 |
| Min. to +2 | 5.7 | 5.2 | 6.2 | 5.5 | 5.7 | 6.1 | 4.6 |
| Min. to 80% | 12.7 | 12.2 | 13.7 | 12.8 | 13.8 | 13.7 | 11.7 |
| Min. to 85% | 13.9 | 13.6 | 15.0 | 14.1 | 14.7 | 15.2 | 13.2 |
| Min. to 90% | 15.7 | 15.5 | 16.9 | 15.7 | 16.6 | 17.1 | 15.3 |
| Min. to 95% | 18.2 | 18.5 | 19.9 | 18.2 | 19.7 | 19.7 | 18.6 |
| Mooney Scorch at 250° F. | | | | | | | |
| Low | 22.0 | 21.5 | 20.0 | 21.0 | 20.5 | 20.5 | 21.5 |
| Min. to +3 | 14.6 | 13.6 | 16.3 | 14.5 | 15.0 | 14.9 | 14.2 |
| Min. to +5 | 15.3 | 14.4 | 17.1 | 15.4 | 15.7 | 15.8 | 15.0 |
| Min. to +10 | 16.1 | 15.4 | 18.0 | 16.4 | 16.6 | 16.7 | 15.9 |
| Physical Properties of "Best Cure" Based on 85% Rheometer | | | | | | | |
| Time at 280° F. | 14 | 14 | 15 | 14 | 15 | 15 | 13 |
| Tensile | 4050 | 4000 | 3800 | 3800 | 3850 | 3550 | 3800 |
| Elongation | 670 | 690 | 680 | 680 | 670 | 670 | 670 |
| 300% Modulus | 630 | 590 | 560 | 600 | 600 | 540 | 520 |
| 400% Modulus | 1150 | 1080 | 1010 | 1100 | 1110 | 980 | 920 |
| Shore A | 45 | 45 | 44 | 45 | 45 | 44 | 43 |
| Oven Aged 70 hours at 212° F. | | | | | | | |
| Tensile | 2050 | 2550 | 2750 | 2350 | 1925 | 2525 | 1900 |
| Elongation | 475 | 510 | 515 | 500 | 510 | 540 | 520 |
| Shore A | 48 | 51 | 51 | 48 | 48 | 47 | 42 |
| Oven Aged 30 days at 158° F. | | | | | | | |
| Tensile | 2850 | 3175 | 3250 | 3200 | 2750 | 3250 | 3000 |
| Elongation | 520 | 505 | 530 | 530 | 495 | 490 | 520 |
| Shore A | 51 | 53 | 52 | 53 | 54 | 53 | 52 |
| Oven Aged 12 hours at 250° F. | | | | | | | |
| Tensile | 850 | 1150 | 1525 | 1175 | 825 | 1175 | 650 |
| Elongation | 510 | 555 | 580 | 545 | 500 | 580 | 500 |
| Shore A | 33 | 35 | 37 | 35 | 32 | 33 | 26 |
| Air Bomb Aged 16 hours at 236° F., 80 psi | | | | | | | |
| Tensile | 1325 | 1500 | 1900 | 1475 | 1000 | 1400 | 1100 |
| Elongation | 460 | 470 | 470 | 465 | 410 | 455 | 490 |
| Shore A | 39 | 45 | 45 | 43 | 40 | 43 | 38 |

While certain representative embodiments and details have been shown for the purpose of illustrating the invention, it will be apparent to those skilled in this art that various changes and modifications may be made herein without departing from the spirit or the scope of this invention.

I claim:

1. Compounds comprising the reaction product of a polyphenolic compound having the formula

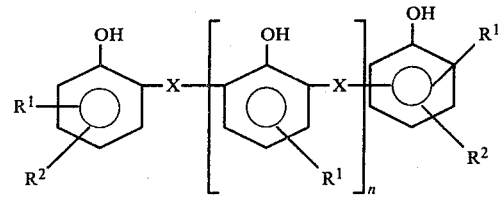

with an ester forming compound of the general formula

(B)

which are then joined through a sulfur atom to form compounds having a general formula selected from the group consisting of

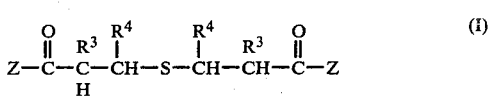

(I)

and

-continued

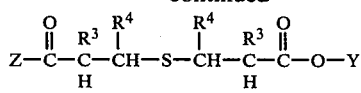
(II)

wherein Z is a phenoxy radical derived from a polyphenolic compound having structural formula (A) and wherein $R^1$ and $R^2$ are the same or different radicals selected from the group consisting of hydrogen, alkyl radicals containing from 1 to 16 carbon atoms, cycloalkyl radicals containing from 5 to 8 carbon atoms, aralkyl radicals containing from 7 to 12 carbon atoms and unsubstituted aryl radicals containing from 6 to 12 carbon atoms, X is the same or different radical selected from the group consisting of (1) cyclic dienes with non-adjacent carbon to carbon double bonds within the ring structure having from 5 to 20 carbon atoms from which the divalent species are prepared and (2) divalent species selected from the group consisting of —S—,

—O—, —CH$_2$— and —S—S— and wherein n is selected from the group consisting of 0 and integers from 1 to 5 and wherein $R^3$ is selected from the group consisting of hydrogen and alkyl radicals having from 1 to 2 carbon atoms, $R^4$ is selected from the group consisting of hydrogen, alkyl radicals having from 1 to 4 carbon atoms, aralkyl radicals having from 7 to 9 carbon atoms, substituted or unsubstituted aryl radicals having from 6 to 8 carbon atoms and wherein V is selected from the group consisting of chlorine, iodine and bromine.

2. Compounds as described in claim 1 wherein $R^1$ is an alkyl radical having from 1 to 2 carbon atoms and is para to a phenolic hydroxyl group.

3. Compounds as described in claim 1 wherein the polyphenolic compounds are treated with from one mole to 0.1 mole of ester forming compound per functional hydroxyl group, more preferably at least one functional hydroxyl group per polyphenolic molecule esterified.

4. Compounds as described in claim 1 wherein the polyphenolic compounds are selected from the group consisting of 2,6-bis-(2-hydroxy-3-tert.butyl-5-methylbenzyl)-4-methylphenol; 2,2'-methylene-bis-(4-methyl-6-tert.butyl phenol); 2,2'-methylene-bis-(4-ethyl-6-tert.butylphenol); 2,2'-thio-bis-(4-methyl-6-tert.butylphenol); 2-(3,5-ditert.butyl 4-hydroxybenzyl)-4-methylphenol; 2-(3,5-ditert.butyl-4-hydroxybenzyl) phenol; 2-(3,5-ditert.butyl-4-hydroxybenzyl)-5-methylphenol, 2,6-bis-(2-hydroxy-3-tert.butyl-5-ethylbenzyl)-4-ethyl phenol and 2-(3,5-ditert.butyl-4-hydroxybenzyl)-4-isopropyl phenol.

5. Compounds as described in claim 1 wherein the cyclic dienes are selected from the group consisting of 1,5-cyclooctadiene; cyclopentadiene; bicyclo[2.2.1]-2,5-heptadiene; dicyclopentadiene; pentacyclo[8.2.1.1$^{4,97}$.0$^{2,99}$.0$^{3,98}$]-tetradeca-5,11-diene, and 1,5,9-cyclododecadiene.

6. Compounds as described in claim 1 wherein the ester forming compounds are selected from the group consisting of acryloyl chloride and methacryloyl chloride.

7. Compounds as described in claim 1 wherein $R^4$ is selected from the group consisting of alkyl radicals having from 1 to 2 carbon atoms and phenyl.

* * * * *